United States Patent
Vedage

[11] Patent Number: 5,973,207
[45] Date of Patent: *Oct. 26, 1999

[54] HYDROGENATION OF META-TOLUENEDIAMINE

[75] Inventor: Gamini Ananda Vedage, Bethlehem, Pa.

[73] Assignee: Air Products and Chemicals, Inc., Allentown, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/127,659

[22] Filed: Sep. 27, 1993

[51] Int. Cl.⁶ .................................................. C07C 209/00
[52] U.S. Cl. ............................................. 564/451; 564/450
[58] Field of Search ...................... 564/450, 451

[56] References Cited

U.S. PATENT DOCUMENTS

| | | | |
|---|---|---|---|
| 2,511,028 | 6/1950 | Whitman | 260/563 |
| 2,606,924 | 8/1952 | Whitman | 260/563 |
| 2,606,925 | 8/1952 | Whitman | 260/563 |
| 2,606,928 | 8/1952 | Barkdall et al. | 260/563 |
| 3,155,724 | 11/1964 | Arhtur | 260/563 |
| 3,347,917 | 10/1967 | Arthur | 260/563 |
| 3,445,516 | 5/1969 | Cross | 564/451 |
| 3,450,759 | 6/1969 | Cross et al. | 260/563 |
| 3,636,108 | 1/1972 | Brake | 260/563 D |
| 3,766,272 | 10/1973 | Brake et al. | 260/563 B |
| 3,856,862 | 12/1974 | Chung et al. | 564/451 |
| 3,914,307 | 10/1975 | Massie | 564/451 |
| 3,959,374 | 5/1976 | Brennan et al. | 260/563 B |
| 4,754,070 | 6/1988 | Casey et al. | 564/451 |
| 4,960,941 | 10/1990 | Vedage et al. | 564/450 |
| 5,026,914 | 6/1991 | Jenkins et al. | 564/451 |
| 5,214,212 | 5/1993 | Whitman | 564/451 |

FOREIGN PATENT DOCUMENTS

| | | |
|---|---|---|
| 839281 | 4/1970 | Canada. |
| 892636 | 2/1972 | Canada. |

*Primary Examiner*—Samuel Barts
*Attorney, Agent, or Firm*—Mary E. Bongiorno; Russell L. Brewer

[57] ABSTRACT

This invention relates to an improved process for the preparation of methylcyclohexane diamine wherein meta-toluenediamine is contacted with hydrogen in the presence of a hydrogenation catalyst. The improvement resides in utilizing a hydrogenation catalyst comprising rhodium carried on a support and carrying out the hydrogenation in the presence of a $C_3$–$C_{10}$ secondary alcohol as a solvent. With the use of rhodium carried on a support as a catalyst, coupled with the use of the secondary alcohol solvent, one obtains high yields with excellent catalyst life.

9 Claims, No Drawings

HYDROGENATION OF META-TOLUENEDIAMINE

FIELD OF THE INVENTION

This invention relates to a process for the hydrogenation of meta-toluenediamines.

BACKGROUND OF THE INVENTION

The hydrogenation of aromatic amines has long been known. Typically, the hydrogenation involves the purification of the feed material by removing various isomers in the feed and/or higher oligomers, as in the case of bridged aromatic amines. These isomers and higher oligomers tend to hydrogenate slowly and many of the impurities in the feed tend to act as catalyst poisons. Representative patents which show the hydrogenation of aromatic compounds, e.g., toluenediamine and bridged aromatic amines are as follows:

U.S. Pat. No. 3,636,108 discloses the process for producing aromatic nitrogen containing compounds such as o-phenylenediamine and methylenedianiline by reacting the aromatic compound with hydrogen at a hydrogen partial pressure of at least 200 psi at a temperature of from 100 to 300° C. A ruthenium catalyst carried on an inert support is used as the hydrogenation catalyst. The process can be carried out in the presence or absence of a solvent and aliphatic and alicyclic hydrocarbon solvents are suggested as being suited for the hydrogenation process.

U.S. Pat. No. 3,450,759 discloses a process for the hydrogenation of toluenediamine and notes the difficulty of the reaction and the resulting low yields. The improved process relies on removing the o-toluenediamines from the feed prior to hydrogenation. Conventional metal catalysts were suggested as effective for the hydrogenation.

U.S. Pat. Nos. 2,511,028; 2,606,924; 2,606,925; 2,606,928; 3,155,724; 3,347,917; 3,766,272; 3,856,862 and 3,959,374 disclose various processes for the hydrogenation of bridged-aronmatic compounds such as methylene-di (aniline). In the processes numerous hydrogenation catalysts such as ruthenium, rhodium, and supports have been suggested for the hydrogenation. Many of the processes disclose the use of an alcohol as a solvent to facilitate the reaction. Representative solvents are set forth in the '826 patent and these include $C_{1-8}$ alkanols. The '917 patent also discloses the use of aliphatic hydrocarbon ethers in addition to alicyclic and aliphatic hydrocarbon solvents and alcohols as a solvent for the catalytic hydrogenation of the aromatic amines.

Canadian patent 892,636 discloses the hydrogenation of toluenediamines to produce the corresponding methane cyclohexanediamine. The patentees point out that a catalyst system comprising a ruthenium hydrogenation catalyst or an alumina supported ruthenium hydrogenation catalyst in combination with the calcium oxide-sodium carbonate mixture are well suited for effecting the hydrogenation of the toluenediamine. The patentees acknowledge that the hydrogenation may be carried out in the presence or absence of solvents such as alcohols and ethers which have been utilized in other prior art.

Canadian patent 839,281 discloses a process for catalytic hydrogenation of various aromatic amines including toluenediamine using a ruthenium catalyst supported on calcium carbonate or a rare earth oxide.

U.S. Pat. No. 4,960,941 discloses a process for the hydrogenation of aromatic amines including both mononuclear and polynuclear aromatic amines to form the corresponding hydrogenated derivative thereof. Toluenediamine is a suggested mononuclear aromatic amine and these include 2,4- and 2,6-toluenediamine and various substituted toluenediamine such as alkylated toluenediamines. The catalyst utilized in the hydrogenation process comprised rhodium carried on a titania support.

Several problems existed with the prior art processes for the hydrogenation of meta-toluenediamines. At moderate pressures (e.g., 1000 psi) the hydrogenation is extremely difficult. The hydrogenation rates are slow and as a consequence higher levels of byproducts are formed. Further, it generally is not possible to obtain more than one or two uses per batch of catalyst as catalyst life is very short.

SUMMARY OF THE INVENTION

This invention relates to an improved process for the hydrogenation of meta-toluenediamine. In the basic process, the meta-toluenediamine is contacted with hydrogen in the presence of a hydrogenation catalyst and a solvent under hydrogenation conditions. The improvement resides in utilizing a catalyst comprising rhodium carried on a support as the hydrogenation catalyst and the utilization of a secondary alcohol as the solvent.

The significant advantages associated with the practice of this invention include: the catalyst system provides enhanced reaction rates at moderate pressures and excellent yield as such moderate reaction pressures as compared to conventional prior art catalysts; the use of the secondary alcohol as a solvent extends the catalyst life and activity; and, lastly, it is not necessary to remove o-toluenediamine impurities from the feed prior to hydrogenation.

DETAILED DESCRIPTION OF THE INVENTION

The feedstock for hydrogenation under hydrogenation condition comprises meta-toluenediamines which include 2,4-toluenediamine; 2,6-toluenediamine and the alkylated 2,4/2,6-toluenediamines where the alkyl substituent is a $C_1-C_6$ alkyl group. Although, hydrogenation of such meta-toluenediamines has been difficult because of various isomers which act as poisons to the hydrogenation catalyst, small amounts e.g., up to about five percent by weight can be present with the meta-toluenediamine feed. Typically, these isomers are the ortho-toluenediamine isomers such as 2,3-toluenediamine; and 3,4-toluenediamine. The meta-feedstock preferably is a mixture of 2,4- and 2,6-toluenediamine and the ratio comprises 65–85 weight parts 2,4-toluenediamine and 15–35 weight parts 2,6-toluenediamine per 100 weight parts of the meta-toluene mixture.

As with conventional processes, the hydrogenation is carried out under liquid phase conditions. Liquid phase conditions are maintained by the use of a solvent, and in this case the solvent is a $C_3-C_{10}$ secondary alkanol. Representative secondary alcohol solvents suited for practicing the invention include isopropanol, 2-butanol, 2-pentanol, 2-n-hexanol, and so forth. Optionally, a small amount of other solvents can be used, e.g., from about 2 to 20 percent by weight of the total solvent used. Other solvents include aliphatic and alicyclic hydrocarbons as well as aliphatic and alicyclic hydrocarbon ethers. Examples include cyclohexane and cyclooctane; tetrahydrofuran, dioxane, and dicyclohexyl ether.

A preferred solvent system is a combination of isopropanol and tetrahydrofuran with the isopropanol being present in from about 10 to 80, most preferably 35 to 65 weight parts per 100 weight parts of total solvent employed in the hydrogenation process. The addition of tetrahydrofuran appears to maintain activity of the rhodium catalyst with the isopropanol extending catalyst life.

The solvent is incorporated into the hydrogenation process in an amount generally from about 10 to 80 weight percent of the feed aromatic amine introduced into the reaction vessel. Typically, the solvent is used at levels from about 75 to about 200 percent by weight of the meta-toluenediamine feed material. Under some circumstances solvent amounts as high as 1,000 to 2,000 percent by weight based upon the weight of the toluenediamine may be used, although no significant benefit have been ascertained.

The hydrogenation generally is carried out as a batch process, although it is possible to operate under continuous conditions. Temperatures for such hydrogenation processes range from about 130 to 220° C. with preferred temperatures of from about 140 to 195° C. Hydrogen partial pressures necessary for effecting hydrogenation of the meta-toluenediamine feedstock range from about 500 to 4,000 psig, although modest pressures from 800 to 2,500 psig can be utilized.

The catalyst used in effecting the hydrogenation is a rhodium metal carried on a support. The rhodium is combined with the support in a ratio of about 1 to 25 weight parts rhodium per 100 weight parts of support and preferably from about 3 to 8 parts rhodium per 100 parts support. At these levels a catalyst level (metal plus support) from 0.1 to 10% by weight of the toluenediamine is used in the hydrogenation of meta-toluenediamine. Typically, the catalyst will be used at a concentration of about 0.5 to 5% by weight. The support may be a conventional support, although titania and alumina are preferred.

Other metals optionally carried on the same or a separate support may be used in combination with the rhodium and they may be incorporated onto the support or added as a separate catalyst system carried on its own support. Representative examples of cocatalysts include ruthenium on alumina; palladium on carbon and so forth. However, best results are achieved with the use of rhodium on a titania or alumina support as the catalyst system.

The progress of the hydrogenation of meta-toluenediamine can be followed by observing the amount of hydrogen consumed during the reaction. The reaction is terminated when the amount of hydrogen absorbed is generally equal or nearly equal to the amount necessary to effect complete hydrogenation of the meta-toluenediamine. In general the hydrogenation reaction times for effecting complete reduction of the meta-toluenediamine will range from about 30 to 600 minutes at a catalyst level of from 0.5–5% by weight.

Although not intending to be bound by theory, the inhibition/deactivation of rhodium in a catalyst system is caused by a combination of catalyst surface acidity and the feed impurities (ortho and para) toluenediamine isomers). The inhibitor or catalyst poison is probably produced by an acid catalyzed condensation of ortho and para toluenediamine which results in a strong aromatic ring adsorption with the catalyst sites. For meta-toluenediamine to be successfully hydrogenated, using rhodium on alumina or rhodium on carbon, in the absence of a secondary alcohol solvent as the catalyst, the feed meta-toluenediamine has to be freed of feed impurities as represented by ortho and para toluenediamine.

Several explanations can be advanced for the enhanced effectiveness of secondary alcohols as solvents or cosolvents in the rhodium catalyzed hydrogenation process. One reason generally recognized by the art is that solvents are relatively inert and serve to remove a polymeric buildup on the catalyst surface during the hydrogenation reaction. To a degree, secondary alcohols function in the same manner as other solvents, i.e., the presently remove polymeric buldup on the catalyst. Although this rationale is suggestive of catalyst life, that rationale does not necessarily explain the enhanced catalytic activity of secondary alcohols in rhodium catalyzed hydrogenation process vis-a-vis primary and tertiary alcohols as solvents. In terms of catalyst activity, one possible explanation of the unexpected benefit by secondary alcohols is that the secondary alcohols generally are less amenable to carbon monoxide or water formation through decarbonylation or dehydration as are the primary and tertiary alcohols. Carbon monoxide and water formation apparently detract from catalyst performance.

The following examples are provided to illustrate various embodiment of the invention are not intended to restrict the scope thereof. All percentages are expressed as weight percentages unless excepted.

Experimental

Feedstock

A series of runs was carried out using a meta-toluenediamine (meta-toluenediamine) feedstock consisting essentially of about 79–81% 2,4-toluenediamine and 19–21% 2,6-toluenediamine. The feedstock also contained about 0.3% of the 2,3- and 3,4-ortho isomers of toluenediamine and about 1% of other isomers such as a para isomer and the 3,5-meta isomer. Other impurities included nitro bodies such as dinitrotoluene (0.03% or less; 0.1% or less water; 0.05% or less toluidines and 3 to 10 parts per million (ppm) $SO_4^{-2}$.

General Experimental Procedure

A 300 cc autoclave was charged with 125 g of tetrahydrofuran (THF). To that, the catalyst was added and the autoclave was sealed and purged with nitrogen followed by hydrogen. The autoclave was then pressurized with hydrogen to 1200 psi and heated to 190° C. The catalyst was reduced at 190° C. for 2 hrs and then cooled to room temperature. After removing the THF, 50 gms of meta-toluenediamine and 75 gms of solvent was added to the reactor. The autoclave was purged with nitrogen followed by hydrogen and then pressurized to a preselected level with hydrogen. The autoclave was heated to 190° C. with stirring and the pressure was maintained by addition of hydrogen from a ballast tank. When the reaction was over the autoclave was cooled to room temperature. The reaction product was analyzed by capillary GC using a method previously calibrated for the materials involved.

Example 1

Hydrogenation of Meta-Toluenediamine and TDA Isomers in Tetrahydrofuran; Conventional Solvent The above meta-toluenediamine feedstock and general experimental procedure was used to hydrogenate meta-toluenediamine 2,4- and 2,6-TDA feedstocks. Table 1 sets forth reaction conditions and results.

TABLE 1

Hydrogenation of 30% Meta-TDA/THF in a 300 cc Batch Reactor at 850 psi Pressure and 180° C.

| Catalyst | Wt %[a] | Reaction Time (min) | MCHD[b] | Deam Product[c] | Heavies[d] | Conversion[e] | Feed |
|---|---|---|---|---|---|---|---|
| 5% Rh/Al$_2$O$_3$ | 1.5 | 600 | 17 | 18 | 6 | 41% | Meta-TDA |
| 5% Rh/Al$_2$O$_3$ | 1.5 | 180 | 39 | 59 | 2 | 100% | 2,6 TDA |
| 5% Rh/Al$_2$O$_3$ | 1.5 | 400 | 51 | 35 | 14 | 100% | 2,4 TDA |

[a]weight percent expressed as a percentage of TDA in the reactor
[b]MCHD = methylcyclohexanediamine
[c]Deam Product = methylcyclohexaneamine
[d]Heavies = condensation products of MCHD
[e]Conversion = percentage TDA hydrogenated The above Table 1 shows that in 180 min, 2,6-TDA was completely hydrogenated while 2,4-TDA took about 400 min for complete hydrogenation. The hydrogenation of the 80/20 meta-toluenediamine feed was slow and incomplete even after 600 min at 180° C. These data clearly show the inhibition in hydrogenation rate in the meta-toluenediamine feedstock is due to feed impurities. Substantial deamination occurred at the low hydrogenation pressure.

Example 2

Comparative Hydrogenation of Meta-TDA Comparison of Supports in THF

To avoid problems encountered with Rh/Al$_2$O$_3$ catalysts at low pressures (1000 psi), meta-toluenediamine was hydrogenated at 2500 psi (high pressure) with rhodium catalysts on different supports.

that at high pressures catalyst deactivation is support related and a catalyst such as Rh/TiO$_2$ gives more stable use to use performance than Rh/Al$_2$O$_3$ or Rh/C catalyst.

Higher pressures and catalyst loading did as expected, enhance reaction rates as evidenced by the shorter reaction times.

Example 3

Comparative Meta-TDA Hydrogen with Rh/TiO$_2$ and Rh/Al$_2$O$_3$

Meta-toluenediamine in THF (42%) was successfully hydrogenated using Rh/TiO$_2$ catalyst under mild hydrogenation conditions (1250 psi pressure).

TABLE 2

Hydrogenation of 42% Meta-TDA in THF at 2 wt % Catalyst Loading and 2500 psi Over Rhodium Catalysts

| Metal or Catalyst Support | Temp ° C. | Uses | Induction[a] Period (Mins) | Total Rxn Time (Mins) | Deaminated[c] Product | MCHD[b] | Heavies[d] |
|---|---|---|---|---|---|---|---|
| Rh/Al$_2$O$_3$ | 170 | 1 | 0 | 260 | 15.3 | 82.0 | 2.6 |
|  | 175 | 2 | 120 | 420 | 21.2 | 71.9 | 4.2 |
|  | 175 | 3 | 200 | 500 | 26.4 | 66.3 | 7.3 |
|  | 185 | 4 | 600 | 600 | - No Hydrogenation - | | |
| Rh/TiO$_2$ | 170 | 1 | 0 | 140 | 11.2 | 86.4 | 2.4 |
|  | 170 | 2 | 0 | 170 | 15.1 | 81.9 | 3.1 |
|  | 175 | 3 | 30 | 210 | 19.2 | 74.8 | 6.0 |
|  | 175 | 4 | 45 | 250 | 20.6 | 70.2 | 9.2 |
| Rh/C | 170 | 1 | 540 |  | - No Hydrogenation - | | |

[a]Induction Period = There is no hydrogen consumption during this period.
[b]Same as Table 1.
[c]Same as Table 1.
[d]Same as Table 1.

As shown in Table 2, the Rh/Al$_2$O$_3$ catalyst did not show any induction period in the first use, but developed an induction period in subsequent uses and was completely deactivated by the fourth use. On the other hand, a 5% Rh/TiO$_2$ catalyst hydrogenated meta-toluenediamine without any problems. In the fourth use, the reaction time was 250 min with a modest 45 minute induction period. When a more acidic support, e.g., carbon was used, there was no hydrogenation activity in 540 minutes. These results suggest

TABLE 3

Activity at 1200 psi pressure and 3 wt % Catalyst Loading at 150° C.

| Catalyst | Use | Reaction Time | Deams[c] | Yield[b] MCHD | Heavies[d] |
|---|---|---|---|---|---|
| 5% Rh/Al$_2$O$_3$ | 1 | 600 min | 24% | 67% | 9% |
|  | 2 |  |  | No reaction |  |

TABLE 3-continued

Activity at 1200 psi pressure and 3 wt % Catalyst Loading at 150° C.

| Catalyst | Use | Reaction Time | Deams[c] | Yield[b] MCHD | Heavies[d] |
|---|---|---|---|---|---|
| 5% Rh/TiO$_2$ | 1 | 220 min | 12.3% | 82.2% | 5.4% |
|  | 2 | 520 min | 16.4% | 76.8% | 6.8% |
|  | 3 | 1360 min | 22.1% | 70.0% | 7.9% |

[b]Same as Table 1.
[c]Same as Table 1.
[d]Same as Table 1.

As shown in Table 3, Rh/Al$_2$O$_3$ catalyst was completely deactivated after the first use. On the other hand, the Rh/TiO$_2$ catalyst gave 3 successive uses but it also deactivated rapidly. Deamination was fairly high at the low (1200 psi) pressure.

Example 4

Hydrogenation Using Rhodium Catalyst Comparison of Solvents

The general experimental procedure of Example 1 was repeated using Rh/TiO$_2$ as a catalyst, except various solvents were compared for the hydrogenation process. The conditions and results are set forth in Table 4.

TABLE 4

Hydrogenation of 42% Meta-TDA at 148° C. and 1250 psi using 3 wt % of 5% Rh/TiO$_2$ Catalyst

| Solvent | Use | Reaction Time (min) | Deams[c] % | Heavies[d] % | MCHD[b] % | N-alkyl MCHD |
|---|---|---|---|---|---|---|
| None | 1 | 400 | 13.0 | 9.5 | 77.5 | — |
|  | 2 | 700 | 16.3 | 12.7 | 71.0 | — |
| Isopropanol (IPA) | 1 | 240 | 4.6 | 0.4 | 83.9 | 11.0 |
|  | 2 | 260 | 8.2 | 0.6 | 72.5 | 18.6 |
|  | 3 | 280 | 9.0 | 0.7 | 64.5 | 25.9 |
| 2-Butanol | 1 | 200 | 15.0 | 4.2 | 77.4 | 3.4 |
|  | 2 | 200 | 16.0 | 4.2 | 76.7 | 3.1 |
|  | 3 | 180 | 15.8 | 5.6 | 76.2 | 3.1 |
| IPA/THF[g] (35/65) | 1 | 300 | 10.5 | 3.7 | 85.0 | 0.8 |
| IPA/THF[g] (65/35) | 2 | 280 | 10.4 | 3.3 | 80.5 | 5.8 |
| IPA/THF[g] (65/35) | 3 | 300 | 11.4 | 3.3 | 79.5 | 6.3 |
| THF | 1 | 220 | 12.3 | 5.4 | 82.2 | — |
| THF | 2 | 520 | 16.4 | 6.8 | 76.8 | — |
| THF | 3 | 1360 | 22.1 | 7.9 | 70.0 | — |
| n-propanol | 1 | 600[e] | 10.4 | 19.3 | 10.4 | 59.7 |
| t-butanol | 1 | 600[f] | 43.6 | 19.0 | 37.4 | >0.1 |
| n-butanol | 1 | 400[f] | 56.7 | <0.1 | 8.7 | 34.6 |

[b]Same as in Table 1.
[c]Same as in Table 1.
[d]Same as in Table 1.
[e]Reaction temperature 175° C.
[f]Reaction temperature 200° C.
[g]IPA = isopropanol.
IPA/THF = 35 weight parts IPA and 65 weight parts THF, and 65 weight parts IPA and 35 weight parts THF Surprisingly, the secondary alcohol solvents gave good rates, high yields of MCHD and less deaminated byproduct. The primary and the tertiary alcohols were not effective as hydrogenating solvents. However, the use of the secondary alcohol, isopropanol, introduced an additional byproduct. This byproduct, N-isopropyl MCHD, was minimized by using an isopropanol/THF (35/65 and 65/35) solvent mixture. With the mixed solvent system, high yields of MCHD and very low amounts of N-alkylated products were obtained. The data also shows that activity is not significantly affected by the ratio of IPA/THF from 35/65 to 65/35. The effectiveness (based on reaction time) of solvents screened were in the order: 2 butanol, isopropanol, isopropanol/THF>THF>>t-butanol, n-butanol.

With secondary alcohol solvents, high yields of MCHD and minimum deactivation of Rh/TiO$_2$ and Rh/Al$_2$O$_3$ catalysts were seen in four uses. Table 4 gives the yield of MCHD and hydrogenating time with use. The data clearly illustrates the superior performance and high yields obtained when secondary alcohol or isopropanol/THF is used as a solvent. Deamination and the heavies formation with this mixed solvent system was about half of that with THF.

In summary, the advantages of secondary alcohol solvents are minimum catalyst deactivation and higher MCHD yields. On the other hand, solvents such as THF give faster catalyst deactivation and lower yields due to higher byproduct formation.

Example 5

The procedure of Example 4 was used except that Rh/Al$_2$O$_3$ was used as the catalyst system. The results are set forth in Table 5.

TABLE 5

Hydrogenation of 42% Meta-TDA/Solvent at 160° C. and 1250 psi using 3 wt % of 5% Rh/Al$_2$O$_3$ Catalyst

| Solvent | Use | Reaction Time (min) | Deams[c] % | Heavies[d] % | MCHD[b] % | N-alkyl MCHD % |
|---|---|---|---|---|---|---|
| Isopropanol | 1 | 220 | 13.1 | 2.1 | 65.1 | 19.7 |
| Isopropanol | 2 | 180 | 13.4 | 1.8 | 66.5 | 18.3 |
| Isopropanol | 3 | 240 | 13.5 | 2.2 | 59.3 | 25.0 |
| Isopropanol/ THF (35/65) | 4 | 340 | 15.2 | 1.8 | 81.2 | 1.8 |
| Isopropanol/ THF (35/65) | 5 | 380 | 15.5 | 2.0 | 79.5 | 3.0 |
| THF | 1 | 600[a] | 24.0 | 9.0 | 67.0 | — |
| THF | 2 | 400[a] | No Hydrogenation | | | |

[a]at 150° C.
[b]Same as in Table 1.
[c]Same as in Table 1.
[d]Same as in Table 1.

The Rh/Al$_2$O$_3$ catalyst in comparison to the Rh/TiO$_2$ catalyst appears to be as effective. Reaction times, although slightly less, are similar, perhaps due to the use of a slightly higher temperature. The use of a secondary alcohol, such as isopropanol, clearly shows a significant advantage over the conventional solvent, THF.

What is claimed is:

1. In a process for the catalytic hydrogenation of meta-toluenediamines to their ring hydrogenated counterparts by contacting a meta-toluenediamine with hydrogen in the presence of a hydrogenation catalyst and a solvent, the improvement which comprises:

utilizing a hydrogenation catalyst consisting essentially of a supported rhodium catalyst, and utilizing a solvent consisting essentially of a secondary C$_3$ to C$_{10}$ alcohol or a combination of a secondary C$_3$ to C$_{10}$ alcohol with tetrahydrofuran.

2. The process of claim 1 wherein the meta-toluenediamine is 2,4-toluenediamine or 2,6-toluenediamine.

3. The process of claim 2 wherein the meta-toluenediamine comprises a mixture of 2,4- and 2,6- toluenediamine and the ratio of 2,4-toluenediamine to 2,6-toluenediamine is from about 65–85 weight parts 2,4-toluenediamine and 15–35 parts 2,6-toluenediamine per 100 weight parts meta-toluene mixture.

4. The process of claim 3 wherein the supported rhodium catalyst is carried on an alumina or a titania support and consists essentially of from about 3 to 8 weight parts rhodium per 100 weight parts support.

5. The process of claim 4 wherein the hydrogen pressure ranges from about 800 to 2500 psig.

6. The process of claim 4 wherein the secondary $C_3$ to $C_{10}$ alcohol solvent consists essentially of isopropanol.

7. The process of claim 4 wherein the secondary $C_3$ to $C_{10}$ alcohol solvent consists essentially of 2-butanol.

8. The process of claim 4 wherein the solvent consists essentially of from 10–80 weight parts isopropanol and 20–90 weight parts tetrahydrofuran per 100 weight parts total solvent.

9. The process of claim 8 wherein the solvent consists essentially of from 35–65 weight parts isopropanol and 35–65 weight parts tetrahydrofuran.

* * * * *